(12) United States Patent
Pettit et al.

(10) Patent No.: US 6,437,128 B1
(45) Date of Patent: Aug. 20, 2002

(54) CRIBROSTATINS 3-5

(75) Inventors: George R. Pettit, Paradise Valley; John C. Knight, Phoenix, both of AZ (US)

(73) Assignee: Arizona Board of Regents, Tempe, AZ (US)

( * ) Notice: Subject to any disclaimer, the term of this patent is extended or adjusted under 35 U.S.C. 154(b) by 0 days.

(21) Appl. No.: 09/785,854

(22) Filed: Feb. 16, 2001

(51) Int. Cl.$^7$ .................... C07D 241/38; C07D 217/16; A61P 35/00
(52) U.S. Cl. ........................ 544/342; 546/147
(58) Field of Search ............... 544/342; 546/147

(56) References Cited

U.S. PATENT DOCUMENTS 4,372,947 A * 2/1983 Arai et al. .................. 424/121

OTHER PUBLICATIONS

Balasubramanian, B.N. et al, "Recent Developments in Cancer Cytoxics" in "Annual Reports in Medicinal Chemistry, vol. 33", Academic Press, San Diego, 1998, pp. 151–159.*

Draetta, G. and Pagano, M. in "Annual Reports in Medicinal Chemistry, vol. 31", 1996, Academic Press, San Diego, p241–246.*

Salmon, S.E. et al "Principles of Cancer Therapy" in "Cecil Textbook of Medicine, 20th Edition", W.B. Saunders, Philadelphia, 1996, pp. 1036–1049.*

* cited by examiner

Primary Examiner—Mukund Shah
Assistant Examiner—Thomas C McKenzie
(74) Attorney, Agent, or Firm—Richard R. Mybeck

(57) ABSTRACT

The blue marine sponge Cribrochalina sp., collected in the Republic of Maldives was found to contain new cell growth inhibitors denominated cribrostatin 3, cribrostatin 4 and cribrostatin 5 which were found to be active against the NCI human melanoma panel and the P388 marine lymphocytic cell lines employed by the U.S. National Cancer Institute. Structural determination of all three substances were accomplished utilizing high yield NMR (400 MHz) and mass spectral studies. Cribrostatins 3–5 were also found to possess significant antibacterial and antifungal activity.

4 Claims, 2 Drawing Sheets

CRIBROSTATINS 3-5

This research was funded in part by Outstanding Investigator Grant CA44344-01-11 awarded by the Division of Cancer Treatment, National Cancer Institute, DHHS. The United States government may have certain rights to this invention.

The present invention relates generally to the isolation and structural elucidation of new compounds herein denominated Cribrostatin 3, Cribrostatin 4 and Cribrostatin 5, which are obtained from Cnbrochalina sp., (Niphatidae faily, Haplosclerida order, Demospongiae class) found off of remote islands in the Republic of Maldives.

BACKGROUND OF THE INVENTION

In early research devoted to the first systematic investigation of marine animals as new sources of potential anticancer drugs, the phylum Porifera rapidly became of increasing importance. Subsequent detection of antineoplastic activity in some of these sponge species led to the isolation of such cell growth inhibitory compounds, as macrocyclic lactones, pyrroles, peptides and proteins. Meanwhile the isolation of heterocyclic marine sponge constituents such as pyrroles, imidazoles, oxazoles, indoles, pyndines, quinolizidines, pteridines, acridines, other nitrogen systems and quinones has been rapidly accelerating. So far ten isoquinolinequinones have been isolated from blue species of the sponge genera Reniera and Xestospongia. In 1986, an exploratory survey of marine Porifera off remote islands in the Republic of the Maldives was conducted which located a deep blue colored specimen of Cribrochaina sp. (Haplosclerida order) that afforded an orange ethanol extract. The encrusting sponge was found in areas of strong (and dangerous) currents to −45 m in the South side of East reef passages and yielded an ethanol extract that provided 40% life extension (at mg/kg) against the U.S. National Cancer Institute's in vio murine P388 lymphocytic leukemia (PS system). Bioassay directed isolation using the in vitro PS leukemia led to the discovery of new cytostatic isoquinoline-quinones designated cribrostatin 1 and cribrostatin 2, described and claimed in U.S. Pat. No. 5,514,689.

Continued investigation of cancer cell growth inhibitory constituents of the blue marine sponge Cribrochalina sp. has led to the further discovery of cribrostatins 3 (4a), 4 (5), and 5 (4b) in $10^{-5}$ to $10^{-7}$ percent yields. The structure of cribrostatin 3 (4a) was determined by results of high field (500 MH) $^1$H- and $^{13}$C-nmr and high resolution mass spectral interpretations. The same general approach to the structures of cribrostatins 4 (5) and 5 (4b) was completed by x-ray crystal structure determinations. Cribrostatins 3,4 and 5 provided significant cancer cell line inhibitory activities. In addition, the newly isolated cribrostatins 3,4 and 5 also display antibacterial and/or antifungal activities.

BRIEF SUMMARY OF THE INVENTION

The present invention relates to the isolation and structural elucidation of three new isoquinolinequinones herein denominated cribrostatin 3, cribrostatin 4 and cribrostatin 5, which are obtained from Cribrochalina sp. (Haplosclerida order) found off of remote islands in the Republic of the Maldives. All three isolates demonstrated cytostatic properties using $ED_{50}$ and NCI human cell lines tests. The general structural formulas are shown below:

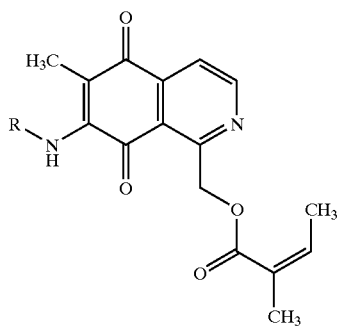

4a, R = H, Cribrostatin 3
b, R = CH$_3$, Cribrostatin 5

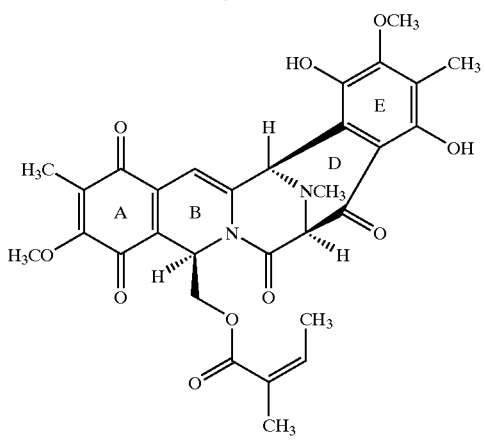

5, Cribrostatin 4

Accordingly, the primary object of the present invention is the isolation and elucidation of new antineoplastic and antibacterial and/or antifuingal agents denominated herein as "Cribrostatin 3", "Cribrostatin 4" and "Cribrostatin 5".

A further object of the present invention is to isolate and identify new natural substances which can be utilized in the treatment and management of those neoplastic diseases which are characterized by an uncontrolled cell growth and have an established correlation to the NCI protocol for P388 murine lymphocytic leukemia and human cancer cell lines.

Another object of the present invention is to elucidate unequivocally the structure of a newly discovered isoquinolinequinone denominated "cribrostatin 3" so as to provide a readily discernible target for further synthetic endeavors.

Another object of the present invention is to elucidate unequivocally the structure of a newly discovered isoquinolinequinone denominated "cribrostatin 4" so as to provide a readily discernible target for further synthetic endeavors.

Still another object of the present invention is to elucidate unequivocally the structure of a newly discovered isoquinolinequinone denominated "cribrostatin 5" so as to provide a readily discernible target for further synthetic endeavors.

These and still further objects as shall hereinafter appear are readily fulfilled by the present invention in a remarkably unexpected manner as will be readily discerned from the following detailed description of an exemplary embodiment thereof

DESCRIPMON OF THE PREFERRED EMBODIMENT

Figure 1:
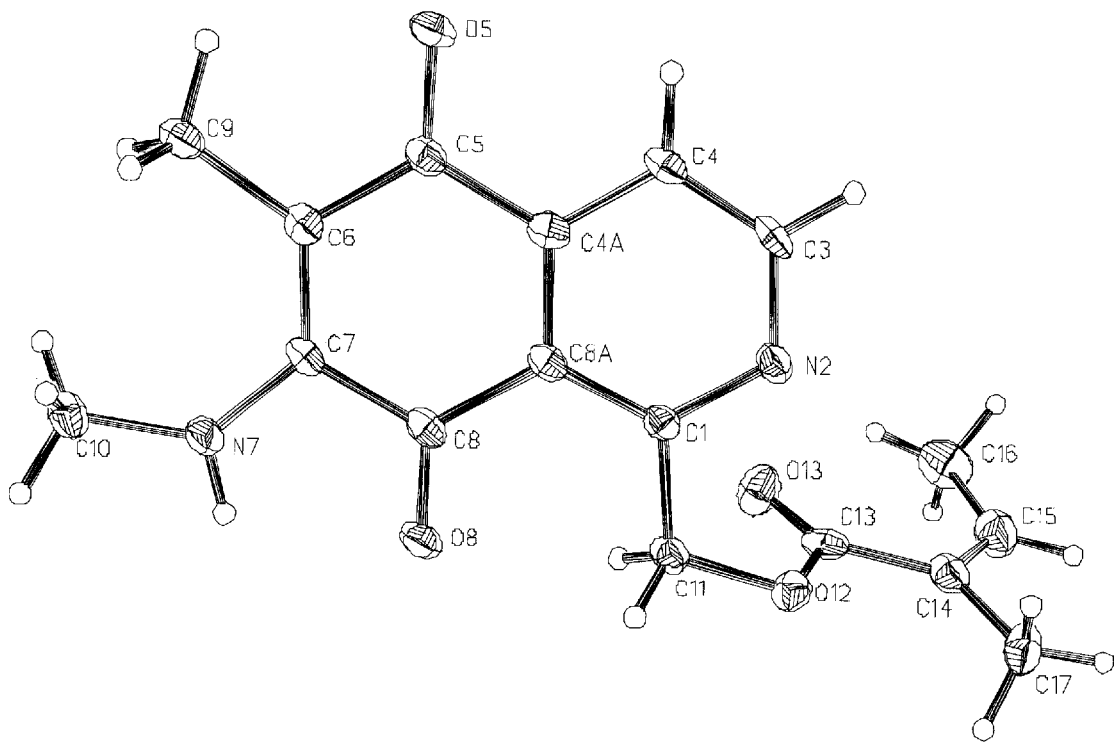
FIG. 1 is the crystal structure of cribrostatin 5.

As indicated above, the present invention relates generally to the field of Antineoplastic Agents and more particularly to Isolation and Structural Elucidation of Cribrostatins 3, 4, and 5 from Cribrochalina sp. (Porifera) found near the Republic of Maldives.

In 1986, we began investigating the blue sponge Cribrochalina sp. collected in reef passages in the Republic of Maldives. Six years later, we reported the isolation of cribrostatin 1 (1), cribrostatin 2 (2a), mimosamycin (2b), renierone (3a), and its O-demethyl derivative (3b). (See: Pettit, G. R.; Collins, J. C.; Herald, D. L.; Doubek, D. L.; Boyd, M. R.; Schmidt, J. M.; Hooper, J. N. A; Tackett, L. P. Can. J. Chem. 1992, 70, 1170–1175). Subsequently, both cribrostatins 1 and 2 have been prepared by synthesis. (See: Nakahara, S.; Numata, R.; Tanaka, Y.; Kubo, A. Heterocycles 1995, 41, 651–654). While our initial summary (See: Pettit, G. R; Collins, J. C.; Herald, D. L.; Doubek, D. L.; Boyd, M. R.; Schmidt, J. M.; Hooper, J. N. A.; Tackett, L. P. Can. J. Chem. 1992, 70, 1170–1175) of the cribrostatins represented one of only a few known chemical investigations of the Cibrochalina genus (previously focused on C. dura and C. vasculum), in the interim interest has been expanding, especially with the acetylenic alcohols contained in C vasculum. (See: Aiello, A.; Fattorusso, E.; Menna, M.; Pansini, M. J. Nat. Prod. 1992, 55, 1275–1280: KuLkni, B. A.; Chattopadhyay, A.; Mamdapur, V. R. Coll. Czech. Chem. Commun. 1993, 58, 1711–1713: Kulkarni, B. A.; Chattopadhyay, S.; Chattopadhyay, A.; Mamdapur, V.R J. Org. Chem. 1993, 58, 5964–5966: Hallock, Y. F.; Cardellina, J. H. II; Balaschak, M. S.; Alexander, M. R.; Prather, T. R.; Shoemaker, R. H.; Boyd, M. R. J. Nat. Prod. 1995, 58, 1801–1807: Dai, J-R.; Hallock, Y. F.; Cardellina, J. H. II; Boyd, M. R. J. Nat. Prod. 1996, 59, 88–89: Ohtani, T.; Kikuchi, K.; Kamezawa, M.; Hamatani, H.; Tachibana, J.; Totani, T.; Naoshima, Y. J. Chem. Soc. Perkin Trans 1 1996, 10, 961–962). Other studies have been concerned with antifungal pyridine derivatives (See: Matsunaga, S.; Shinoda, K.; Fusetani, N. Tetrahedron Lett., 1993, 34, 5953–5954) and marine alkaloids (See: Crews, P.; Cheng, X-C.; Adamczeski, M.; Rodriguez, J.; Jaspars, M.; Schmitz, F. J.; Traeger, S. C.; Pordesimo, E. O. Tetrahedron 1994, 50, 13567–13574), of C. sp., the cancer cell growth inhibitory cyclic hexapeptide kapakahine B (See: Nakao, Y.; Yeung, B. K. S.; Yoshida, W. Y.; Scheuer, P.; Kelly-Borges, M. J. Am. Chem. Soc. 1995, 117, 8271–8272), other cyclic peptides See: Yeung, B. K. S.; Nakao, Y.; Kinnel, R. B.; Camey, J. R.; Yoshida, W. Y.; Scheuer, P. J.; Kelly-Borges, M. J. Org. Chem. 1996, 61, 7186–7173: Yeung, B. K. S.; Hamann, M. T.; Scheuer, P. J.; Kelly-Borges, M. Tetrahedron 1994, 50, 12593–12598) and a 19-norpregnane glycocide from C. olemda[6d], as well as isolation of a cyclopropyl-ring containing sterol from C. vasculum. (See: Giner, J. L.; Djerassi, C. Steroids 1992, 57, 258–261). After our initial investigation of the Maldives Cribrochalina sp., evidence accumulated suggesting the presence of other cancer cell growth inhibitory constituents. As part of that extended study, we isolated and elucidated the structures of three new biologically active components designated cribrostatins 3 (4a), 4 (5), and 5 (4b).

The fractions obtained from the 1988–89 recollection of Cribrochalina so. (See: Pettit, G. R.; Collins, J. C.; Herald, D. L.; Doubek, D. L.; Boyd, M. R.; Schmidt, J. M.; Hooper, J. N. A.; Tackett, L. P. Can. J. Cheim. 1992, 70, 1170–1175) beginning with the 195 g dichloromethane partition fraction were re-examined guided by bioassay results using the murine P388 lymphocytic leukemia. Further fractional recrystallization of constituents accompanying the original isolation of cribrostatin 1 (1) afforded the new isoquinoline quinone 4a($2.8 \times 10^{-5}$% yield, PS $ED_{50}$ 2.5 µg/ml). Application of high speed countercurrent distribution procedures (See: Schaufelberger, D. E.; Pettit, G. R. J. Liquid Chromatog. 1989, 12, 1909–1917: Pettit, G. R.; Kamano, Y.; Schaufelberger, D. E.; Herald, C. L.; Blumberg, P. M.; May, S. W. J. Liquid Chromatog. 1989, 12, 553–561) employing an Ito Coil Planet centrifuge, to fractions accompanying the original isolation of renierone (3a) afforded cribrostatin 5 (4b, $9 \times 10^{-7}$% yield, PS $ED_{50}$ 0.045 µg/ml) When the fraction that originally provided mimosamycin (2b) was further separated by high speed countercurrent distribution, cribrostatin 4 (5, $1.4 \times 10^{-5}$% yield, PS $ED_{50}$ 25 µg/ml) was isolated.

The structural assignments of cribrostatins 3,4 and 5 were established using spectral and X-ray methods. The basic atom connectivity of cribrostatin 5 (4b) was established via X-ray crystal structure determination. The quinone carbonyl groups could be readily assigned from bond distances (C5–O5, 1.256 Å and C8–O8, 1.236 Å). The remaining atomic assignments of cribrostatin 5 were based upon bond distances, and the observed spectral and nmr data similarities between 4b and a previously reported renierone (See: Davidson, B. S. Tetrahedron Lett. 1992, 33, 3721–3724: He, H. Y.; Faulkner, J. D. J. Org. Chem. 1989, 54, 5822–5824: Frincke, J. M.; Faulkner, D. J. J. Am. Chem. Soc. 1982, 104, 265–269) (3a). The latter is an analogue of cribrostatin 5, in which the ring substituent at C7 is an O-methyl, instead of an N-methyl. The model used for cribrostatin 5 (4b) is shown in FIG. 1 (X-ray numbering system). Final least-squares refinement of this structure resulted in a standard residual $R_1$ of 0.0832 for quinone 4b.

The close structural relationship of cribrostatin 3 (4a) to cribrostatin 5 (4b), and cribrostatin 1 (1), was apparent from the similarities observed in the $^1$H- and $^{13}$C-nmr (See: Table 1) and mass spectral data exhibited by these substances. Such observations, coupled with the fact that the mass spectra showed only a 14 amu difference between cribrostatin 3 and cribrostatin 5, led to the ready solution for cribrostatin 3 as the N-demethylated derivative of quinone 4b.

Figure 2:
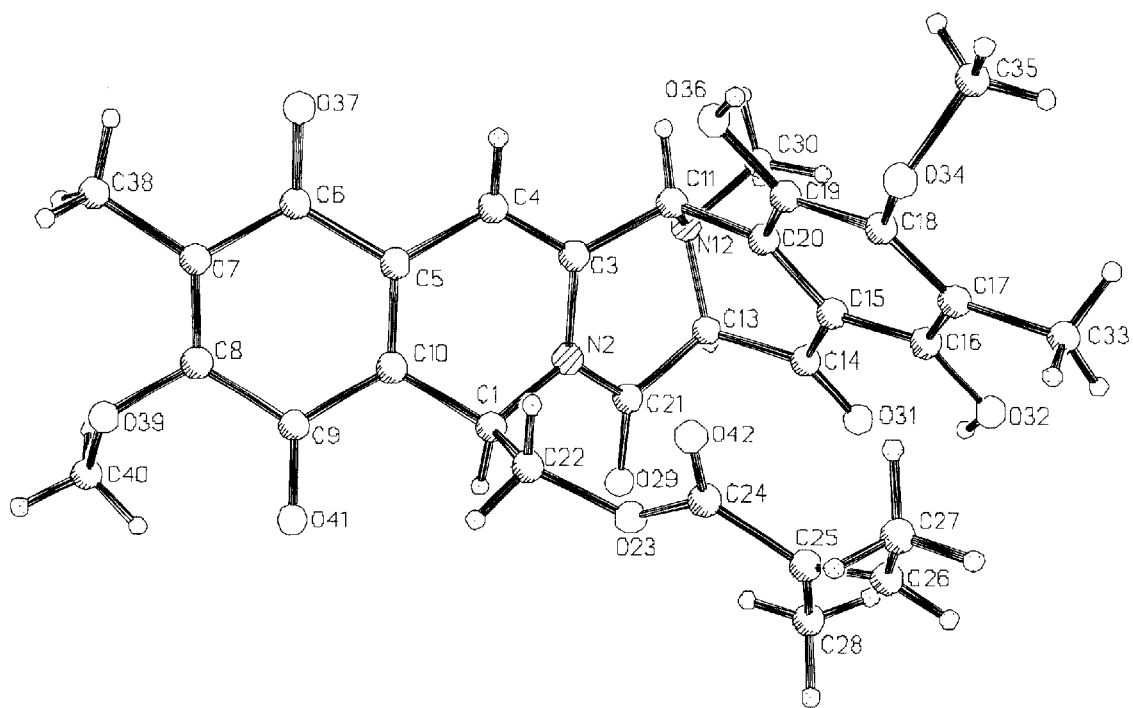
FIG. 2 is the solid state conformation of cribrostatin 4.

On the other hand, the structure of cribrostatin 4 (5) proved to be far more challenging and had to rely almost solely on a detailed X-ray crystal structure determination for unequivocal assignment. Crystals of this compound, which occurred as well-formed, ruby-red prisms, exhibited sufficiently intense anomalous dispersion effects with Cu radiation to allow the assignment of the absolute configuration and complete structure by X-ray diffraction methods. SHELXL (See: "SHELXTL-Version 5.1 (1997)", an integrated suite of programs for the determination of crystal structures from diffraction data, is available from Bruker AXS, Inc., Madison, Wisconsin 53719, USA. This package includes, among others, XPREP (an automatic space group determination program), SHELXS (a structure solution program via Patterson or direct methods), and SHELXL (structure refinement software) refinement of the enantiomer shown in FIG. 2 along with the Flack absolute structure parameter (See: Flack, H. D. Acta Cryst 1983, A39, 876–881: Flack, H. D., Schwarzenbach, D. Acta Cryst. 1988, A44, 499–506) resulted in a Flack parameter value of −0.1 (3). But, refinement of the mirror image of the model shown in FIG. 2 gave a Flack parameter value of +1.1(3). In addition, a slightly larger wR2 value was observed for refinement of the mirror image of the structure shown in FIG. 2, (0.1932 vs. 0.1930). As a consequence, the absolute stereochemistry for the three chiral centers of cribrostatin 4 (using the X-ray numbering system) were assigned as follows: 1R, 11R, 13S. The quinone oxygen atoms in ring A of cribrostatin 4 were readily assigned from bond distances (C6–O37, 1.225A; C9–O41, 1.227A) and were significantly shorter than the phenolic hydroxyl bond distances in ring E (C16–O32, 1.353A; C19–O36, 1.385A). As a consequence, the oxygen atoms in ring E of cribrostatin 4(5) differ from those in ring E of the related renieramycin series (See: Frincke, J. M.; Faulkner, D. J. *J. Am. Chem. Soc.* 1982, 104, 265–269) (6) in that the oxygen atoms occur as a quinone in the latter.

The attractiveness of cribrostatin 4 does not seem limited to its pleasing red color and overall structure, but rather to potential biological properties such as already known for the related renieramycins (See: Davidson, B. S. *Tetrahedron Lett.* 1992, 33, 3721–3724: He, H. Y.; Faulkner, J. D. *J. Org. Chem.* 1989, 54, 5822–5824: Frincke, J. M.; Faulkner, D. J. *J. Am. Chem. Soc.* 1982, 104, 265–269), saframycins (See: Pospiech, A; Bietenhader, J.; Schupp, T. *Microbiology* 1996, 142, 741–746: Kubo, A.; Nakai, T.; Koizumi, Y.; Kitahara, Y.; Saito, N.; Mikami, Y.; Yazawa, K.; Uno, J. *Heterocycles* 1996, 42, 195–211: Saito, N.; Harada, S.; Nishida, M.; Inouye, I.; Kubo, A *Chem. Pharm. Bull.* 1995, 43, 777–782: Cooper, R.; Unger, S. *J. Antibiotics* 1985, 38, 24–30: Arai, T.; Takahashi, K.; Nakahara, S.; Kubo, A. *Experientia* 1980, 36, 1025–1027: Arai, T.; Takahashi, K.; Kubo, A.; Nakahara, S.; Sato, S.; Tamura, C. *Tetrahedron Lett.* 1979, 25, 2355–2358), and ecteinascidins (See: Valoti, G.; Nicoletti, M.; I.; Pellegrino, A.; Jimeno, J.; Hendriks, H.; D'Incalci, M.; Faircloth, G.; Giavazzi, R. *Clin. Cancer Res.* 1998, 4, 1977–1983: Moore, B. M. II; Seaman, F. C.; Wheelhouse, R. T.; Hurley, L. H. *J. Am. Chem. Soc.* 1998, 120, 2490–2491: Corey, E. J.; Gin, D. Y.; Kania, R. S. *J. Am. Chem. Soc.* 1996, 118, 9202–9203: Rinehart, K. L.; Holt, T. G.; Fregeau, N. L.; Stroh, J. G.; Keifer, P. A.; Sun, F.; Li, L. H.; Martin, D. G. *J. Org. Chem.* 1990, 55, 4512–4515). Consequently, cribrostatin 4 (5) is being further pursued.

When tested against a minipanel of human cancer cell lines in our ASU-CRI laboratory, cribrostatins 3–5 showed differing levels of activity (See: Table 3). When tested in the NCI's 60-cell in vitro panel, cribrostatin 3 (4a) and cribrostatin 4 (5) showed mean panel $GI_{50}$ values of 4.27 ($\pm 0.20$)$\times 10^{-6}$ M and 5.01 ($\pm 0.28$)$\times 10^{-6}$ M, respectively (values are averages $\pm$SEM calculated from the 40 cell lines of the NCI panel that yielded $GI_{50}$ values for both 4a and 5). Individual cell line response values are provided in the Experimental.

While cribrostatins 1 (1), 3 (4a), and 5 (4b) exhibited the most potent anticancer cell line activities, cribrostatins 2 (2a) (See: Pettit, G. R.; Collins, J. C.; Herald, D. L.; Doubek, D. L.; Boyd, M. R.; Schmidt, J. M.; Hooper, J. N. A.; Tackett, L. P. *Can. J. Cheim.* 1992, 70, 1170–1175) and 4 (5) had the broadest antimicrobial spectra. Antibiotic activities of cribrostatins 1–5 were determined by disk diffusion using standard protocols (See: National Committee for Clinical Laboratory Standards. 1997. Performance standards for antimicrobial disk susceptibility tests—sixth edition: Approved standard M2-A6. National Committee for Clinical Laboratory Standards, Wayne, Pa.). Cribrostatin 2 (2a), the most potent antibiotic of the cribrostatin series, inhibited opportunistic fungi and a variety of bacteria including clinical isolates of penicillin-resistant *Neisseria gonorrhoeae* and *Streptococcus pneumoniae* (See: Table 4). Mimosamycin, isolated from Reniera (See: Frincke, J. M.; Faulkner, D. J. *J. Am. Chem. Soc.* 1982, 104, 265–269) and Cribrochalina (See: Pettit, G. R.; Collins, J. C.; Herald, D. L.; Doubek, D. L.; Boyd, M. R.; Schmidt, J. M.; Hooper, J. N. A.; Tackett, L. P. *Can. J. Chem.* 1992, 70, 1170–1175) sponge species and from the actinomycete *Streptomyces lavendulae* (See: Fukumi, H.; Kurihara, H.; Hata, T.; Tamura, C.; Mishima, H.; Kubo, A.; Arai, T. *Tetrahedron Lett.* 1977, 43, 3825–3828), has an antimicrobial profile (See: Frincke, J. M.; Faulkner, D. J. *J. Am. Chem. Soc.* 1982, 104, 265–269) similar to cribrostatin 2. This finding is not surprising, given the structural similarities of cribrostatin 2 (2a) and mimosamycin (2b). The cribrostatins warrant further investigation as antibacterial and antifungal agents.

EXPERIMENTAL

General Experimental Methods. Except as now noted, the general experimental procedures employed in our original investigation of Cribrochalina Up. were continued here. (See: Pettit, G. R.; Collins, J. C.; Herald, D. L.; Doubek, D. L.; Boyd, M. R.; Schmidt, J. M.; Hooper, J. N. A.; Tackett, L. P. *Can. J. Chemn.* 1992, 70, 1170–1175). For the present experiments, melting points were measured with an electrothermal digital melting point apparatus (Model 1A9200) and are uncorrected. The Ito Coil Planet centrifuge was supplied by PC, Inc., Potomac, Md. The upper phase of the system, hexane 700: ethyl acetate 300: methanol 150: water 60, was used as the mobile phase at a flow rate of 4.5 ml/min. About 66 ml of lower phase was displaced prior to equilibrium being achieved. The sample (for example 0.133 g of the fraction leading to cribrostatin 4) was dissolved in 12 ml of the lower phase and applied using a loop injection valve. Fractions were pooled on the basis of color and TLC. The IR spectra were obtained using a Matson Instruments 2020 Galaxy series FT-IR. The EIMS data were recorded with MAT 312 mass spectrometer and high-resolution FAB spectra were obtained with a Kratos MS-50 mass spectrometer (Midwest Center for Mass Spectrometry, University of Nebraska, Lincoln, Nebr.). Optical rotation values were recorded employing the Perkin Elmer 241 polarimeter. X-ray data collections were done with an Enraf-Nonius CAD4 diffractometer, unless noted otherwise.

Extraction and Initial Separation of Cribrochalina sp. For details of the 1989 recollection (about 350 kg wet wt.) of the Republic of Maldives blue marine sponge Cribrochalina sp. refer to reference 2. Fractions from the original 195 g dichloromethane soluble fraction prepared from this recollection were further investigated.

Isolation of Cribrostatin 3 (4a). The crude methylene chloride extract (A) was chromatographed on Sephadex LH-20 successively in a.) methanol (Fractions B1-B12) and b.) methylene chloride/methanol 3:2 (fractions C1-C11). The combined fractions C6 and C7 were further fractioned on Sephadex LH-20 in c.) hexane-toluene-methanol (3:1: 1); and d.) hexane-i-propanol-methanol (8:1:1), providing crude cribrostatin 3 (4a) as a red solid (310 mg) which gave small orange-red needles (98 mg) from methylene chloride/methanol: mp 190–192°; P388 $ED_{50}$ 2.5 $\mu$g/mL; ir $v_{max}$ 3400, 1706, 1673, 1606, 1563, 1410, 1397, 1236 cm$^{-1}$ ($CHCl_3$film); Anal. Calcd. for $C_{16}H_{16}N_2O_4$: C 64.00, H 5.37, N 9.33; found C 64.00, H 5.36, N 9.22; HREIM (m/z): 300.1102 ($M^+$calcd. for $C_{16}H_{16}N_2O_4$ 300.1110); LREIMS (m/z): 300, 272, 243, 217, 201, 173, 145, 117, 83, 82 (base). See Table 1 for the $^1$H- and $^{13}$C-nmr.

TABLE 1

The $^1$H- and $^{13}$C-NMR Assignments (500 MHz) for
Cribrostatins 3 (4a) and 5 (4b) in CDCl$_3$ Solution.

| Position[a] | δ-$^1$H (4a) | δ-$^{13}$C (4a) | δ-$^1$H (4b) | δ-$^{13}$C (4b) |
|---|---|---|---|---|
| 1 | | 156.42 | | 156.40 |
| 3 | 8.91 (d., J = 5 Hz) | 154.63 | 8.87 (d., J = 5 Hz) | 154.55 |
| 4 | 7.93(d., J = 5 Hz) | 118.88 | 7.91 (d., J = 5 Hz) | 118.87 |
| 4a | | 140.50 | | 140.88 |
| 5 | | 181.29 | | 182.60 |
| 6 | | 112.81 | | 111.46 |
| 7 | | 145.94 | | 147.35 |
| 8 | | 180.85 | | 182.60 |
| 8a | | 121.80 | | 121.84 |
| 9 (CH2) | 5.74 (s.) | 65.34 | 5.72 (s.) | 65.56 |
| 12 (Angelate C-qu.) | | 127.88 | | 127.90 |
| 13 (Angelate CH) | 6.11 (qu., J = 5 Hz) | 137.91 | 6.1 (qu., J = 5 Hz) | 137.90 |
| N-Me | | — | | 32.85 |
| 6-Me | 2 01 (s) | 9.08 | 2.28 (s.) | 10.78 |
| Ester C = 0 | | 167.96 | | 167.95 |
| 14 (Angelate-Me) | 1.98 (d.) | 15.73 | 1.96 (d.) | 15.75 |
| 15 (Angelate-Me) | 2.02 (m.) | 20.60 | 2.00 (m.) | 20.65 |

[a]Numbering as in Pettit et al.

Isolation of Cribrostatin 4 (5). Fractions C4 and C5 were chromatographed on Sephadex LH-20 in hexane-toluene-methanol (3:1:1) (fractions D1–D15), followed by rechromatography of D4–D7 in hexane-i-propanol-methanol (8:1:1), to give fractions E1–E10. High-speed countercurrent distribution of fraction E6 (133 mg) was performed using an Ito Coil Planet centrifuge. The upper phase of the system, hexane (700): ethyl acetate (300): methanol (150): water (60) was used as the mobile phase, at a flow rate of 4.5 ml/min. About 66 ml lower phase was displaced before equilibrium was achieved. The sample was dissolved in 12 ml of the lower phase and applied using a loop injection valve. Fractions were pooled on the basis of color and TLC (methylene chloride-acetone 9:1). An early-eluting dark wine-red fraction gave a red solid on evaporation, which crystallized from methanol to give cribrostatin 4 (5) as well-formed red prisms (49 mg), mp 190–192° (dec.); P388 ED$_{50}$ 24 μg/mL; ir v$_{max}$ 3429, 1705, 1649, 1566, 1415, 1228, 1155, 754 cm$^{-1}$ (KBr); $_{max}$ (CH$_3$OH): 209 (40,773); 274 (13,679); 359 (8,067); 507 nm (3416). HR-FABMS (M+1)$^+$ 579.1964 (calcd. for C$_{30}$H$_{31}$N$_2$O$_{10}$: 579.1979, error 2.5 ppm) LREIMS (m/z): 580, 578, 550, 521, 467, 465, 453, 451, 439, 437 (base), 423, 409, 396, 234, 220, 206, 192, 114, 100, 83, 56; and $^1$H- and $^{13}$C-nmr (see Table 2 below).

TABLE 2

The $^1$H- and $^{13}$C-NMR (500 MHz) Assignments for
Cribrostatin 4 (5) in CDCl$_3$ Solution.

| Carbon Atom[a] | δ-$^1$H | δ-$^{13}$C | Carbon Atom | δ-$^1$H | δ-$^{13}$C |
|---|---|---|---|---|---|
| 6-Me | 1.93 | 8.59 | 16 | | 119.78 |
| 16-Me | 2.14 | 8.96 | 25 | | 126.56 |
| 27 (angelate Me) | 1.73 (d.) | 15.42 | 6 | | 127.08 |
| 28 (angelate Me) | 1.45 | 19.86 | 9 | | 134.59 |
| N-CH3 | 2.55 | 41.21 | 17 | | 153.33 |
| 11 (CH) | 4.10 | 46.85 | 26(=CH) | 5.9 (qu.) | 139.30 |
| 1 (CH) | 6.18 | 56.17 | 10 | | 139.76 |
| 7-OMe | 3.84 | 61.11 | 18 | | 138.51 |
| 16-OMe | 4.04 | 61.20 | 3 | | 124.18 |
| 22 (CH2) | 3.81, 4.06 | 62.02 | 7 | | 156.31 |
| 13 (CH) | 4.85 | 72.50 | 21 (amide C = 0) | | 161.12 |
| 4 (CH) | 6.22 | 100.04 | 24 (ester C = 0) | | 166.76 |
| 19 | | 108.55 | 8 (qumone C = 0) | | 179.88 |
| 20 | | 119.15 | 5 (quinone C = 0) | | 184.95 |
| 15 | | 156.22 | 14 (Ar.C = 0) | | 192.67 |

[a]Numbering as in Cooper and Unger and Arai et al.

Isolation of Cribrostatin 5 (4b). Fractions B6-B8 were combined and chromatographed twice on Sephadex LH-20 in methylene chloride-methanol (3:2), followed by hexane-toluene-methanol (3:1:1) and hexane-i-propanol-methanol (8:1:1), to give a dark red solid (69 mg). This was subjected to high-speed countercurrent distribution with an Ito Coil Planet centrifuge in hexane (700): ethyl acetate (300): methanol (150): water (60) as described for cribrostatin 4. A dark orange-red solid (9.3 mg) was obtained that gave cribrostatin 5 (4b) as reddish-brown plates (3.0 mg) from methanol-methylene chloride; HRFABMS (M+1)$^+$315.1340 (calcd. for C$_{17}$H$_{19}$N$_2$O$_4$ 315.1345, error 1.5 ppm); LREIMS (m/z): 314, 285, 256, 231, 214, 203, 187, 130, 117, 83, 56; and for the $^1$H- and $^{13}$C-mnr (see Table 1, supra).

Crystal Structure of Cribrostatin 4 (5). Well formed, ruby-red crystals of cribrostatin 4 (5) were obtained via slow evaporation of a methanol solution. A crystal, with approximate dimensions of 0.34×0.18×0.04 mm, was mounted on the tip of a glass fiber with Super Glue. Data collection was performed at 296 (2) K for an orthorhombic system, with all reflections corresponding to slightly more than a complete quadrant (2>130°) being measured using an (ω/2 scan technique. After measurement of each reflection, Friedel reflections were also collected whenever possible. Subsequent statistical analysis of the complete reflection data set using the XPREP (See: "SHELXTL-Version 5.1 (1997)", an integrated suite of programs for the determination of crystal structures from diffraction data, is available from Bruker AXS, Inc., Madison, Wisconsin 53719, USA. This package includes, among others, XPREP (an automatic space group determination program), SHELXS (a structure solution program via Patterson or direct methods), and SHELXL (structure refinement software) program indicated the space group was $P2_12_12_1$. Each asymmetric unit of the cell was found to contain a single molecule of the quinone (5). Crystal data: $C_{30}H_{30}N_2O_{10}$, a=8.394(2), b=17.918(4), c=18.992(4)Å, V=2856.5(10)Å$^3$, (Cu K$_\alpha$)=1.54178 Å, $\rho_c$=1.345 g cm$^{-3}$ for Z=4 and F. W.=578.56, F(000)–1216. After Lorentz and polarization corrections, merging of equivalent reflections and rejection of systematic absences, 4454 unique reflections (R(int)=0.0661) remained, of which 3951 were considered observed ($I_o \leq 2\tau(I_o)$) and were used in the subsequent structure solution and refinement. Linear and anisotropic decay corrections were applied to the intensity data as well as an empirical absorption correction (based on a series of psi-scans). (See: North, A. C.; Phillips, D. C.; Matthews, F. S. Acta Cryst. 1968, A24, 351–359). Structure determination was accomplished with SHELXS. (See: "SHELXTL-Version 5.1 (1997)", an integrated suite of programs for the determination of crystal structures from diffraction data, is available from Bruker AXS, Inc., Madison, Wisconsin 53719, USA. This package includes, among others, XPREP (an automatic space group determination program), SHELXS (a structure solution program via Patterson or direct methods), and SHELXL (structure refinement software). All non-hydrogen atoms for (5) were located using the default settings of that program. The remaining hydrogen atom coordinates were calculated at optimum positions. The latter atoms were assigned thermal parameters equal to either 1.2 or 1.5 (depending upon chemical type) of the Uiso value of the atom to which they were attached and then both coordinates and thermal values were forced to ride that atom during final cycles of refinement. All non-hydrogen atoms were refined anisotropically in a full-matrix least-squares refinement process with SHELXL. (See: "SHELXTL-Version 5.1 (1997)", an integrated suite of programs for the determination of crystal structures from diffraction data, is available from Bruker AXS, Inc., Madison, Wisconsin 53719, USA. This package includes, among others, XPREP (an automatic space group determination program), SHELXS (a structure solution program via Patterson or direct methods), and SHELXL (structure refinement software). The final standard residual Ri value for the model shown in FIG. 2 was 0.0744 (for observed data) and 0.0830 (for all data). The corresponding Sheldrick R values were wR$_2$ of 0.1830 and 0.1930, respectively. The difference Fourier map showed insignificant residual electron density; the largest difference peak and hole being +0.444 and –0.344 e/Å$^3$, respectively. Final bond distances and angles were all within acceptable limits.

Crystal Structure of Cribrostatin 5 (4b). A small, red plate of this compound, obtained via slow evaporation of a methanol-water solution, with approximate dimensions of 0.25×0.23×0.02 mm, was mounted on the tip of a glass fiber. Data collection was performed at 173(2) K on a Siemens Smart system. An initial set of cell constants was calculated from reflections harvested from three sets of 30 frames. These initial sets of frames were oriented such that orthogonal wedges of reciprocal space were surveyed and orientation matrices determined from 80 reflections. Final cell constants were calculated from a set of 1083 strong reflections from the actual data collection. A hemisphere data collection technique was used. A randomly oriented region of reciprocal space was surveyed to the extent of 1.3 hemispheres to a resolution of 0.84 Å. Three major swaths of frames were collected with 0.30 steps in ω. Subsequent statistical analysis of the complete reflection data set using the XPREP (See: "SHELXIL-Version 5.1 (1997)", an integrated suite of programs for the determination of crystal structures from diffraction data, is available from Bruker AXS, Inc., Madison, Wis. 53719, USA. This package includes, among others, XPREP (an automatic space group determination program), SHELXS (a structure solution program via Patterson or direct methods), and SHELXL (structure refinement software) program indicated the space group was P. Crystal data: $C_{17}H_{18}N_2O_4$, a=7.5505(10) Å, b=7.7383(10) Å, c=14.321(2) Å, V=750.5(2) Å$^3$, α=103.491 (2)°, β=92.644(2)°, =111.225(3)°, =(Mo K$_\alpha$)=0.71073 Å, $\rho_c$=1.391 g cm$^{-3}$ for Z=2 and F. W.=314.33, F(000)=332. After Lorentz and polarization corrections, merging of equivalent reflections and rejection of systematic absences, 2407 unique reflections remained ($R_{int}$=0.0358), of which 1173 were considered observed ($I_o$>2$\sigma(I_o)$) and were used in the subsequent structure solution and refinement.

An absorption correction was applied to the data with SADBS. (See: Blessing, R. Acta Cryst. 1995, A51, 33–38). Direct methods structure determination and refinement were accomplished with SHELXTL-V5.1. (See: "SHELXTL-Version 5.1 (1997)", an integrated suite of programs for the determination of crystal structures from diffraction data, is available from Bruker AXS, Inc., Madison, Wisconsin 53719, USA. This package includes, among others, XPREP (an automatic space group determination program), SHELXS (a structure solution program via Patterson or direct methods), and SBELXL (structure refinement software). All non-hydrogen atoms for 4b were located using the default settings of that program. Although the overall connectivity pattern of the non-hydrogen atoms in the structure could be readily established from the data, the low observed data-to-parameter ratio did not allow an unambiguous assignment of all the individual atomic species in 4b. These atomic assignments were determined instead via correlation of cribrostatin 5 to closely related derivatives (See: Pettit, G. R.; Collins, J. C.; Herald, D. L.; Doubek, D. L.; Boyd, M. R.; Schmidt, J. M.; Hooper, J. N. A.; Tackett, L. P. Can. J. Chein1992, 70, 1170–1175: Frincke, J. M.; Faulkner, D. J. J. Am. Chem. Soc. 1982, 104, 265–269: McIntyre, D. E.; Faulkner, D. J.; Van Engen, D.; Clardy, J. Tetrahedron Lett 1979,43, 4163–4166; Kubo, A.; Namahara, S. J. Am. Chem. Soc. 1981, 29, 595–596: Kubo, A.; Nakahara, S.; Inaba, K.; Kitahara, Y. Can. Pharm. Bull. 1986, 34, 4056–4068), taking i nto account the interatomic bond distances, along with snr and mass spectral data observed for this compound. Since the quality of data precluded the direct determination of hydrog en atom positions, the remaining hydrogen atom coordinates were cal culated at optimum positions using the program SHELXL. (See: "SHELXTL-Version 5.1 (1997)", a n integrated suite of programs for the determination of crystal structures from diffraction data, is available from Bruker AXS, Inc., Madison, Wisconsin 53719, USA. This package includes, among others, XPREP (an automatic space group determination program), SHELXS (a structure solution program via Patterson or direct methods), and SHELXL (structure refinement software). These latter atoms were assigned thermal parameters equal to either 1.2 or 1.5 (depending upon chemical type) of the Uiso value of the atom to which they were attached, then both coordinates and thermal values were forced to ride that at om during final cycles of ref inement. All non-hydrogen atoms were refined anisotropically in a full-matrix least-squares refinement process. The final standard residual Ro value for the model shown in FIG. 1 was 0.0832 (for observed data) and 0.1729 (for all data). The corresponding Sheldrick R values were $wR_2$ of 0.1669 and 0.2010, respectively. The difference Fourier m ap showed insignifican t residual electron density; the largest difference peao and hole being +0.332 and −0.399 e/Å$^3$, respectively. Final bond distances and angles were all within acceptable limits.

Testing of Compounds in the NCI 60-Cell Screen. Cribrostatin 3 (4a) and cribrostatin 4 (5) were tested comparatively in the NCI 60-cell screen. Cribrostatin 5 (4b) was not included in this testing due to insufficient supply. Each compound was tested in quadruplicate using an upper concentration limit of $10^{-5}$ M and five, logio-spaced dilutions, otherwise using the standard NCI protocol. The 40 cell lines that gave $GI_{50}$ values for both compounds are listed as follows, along with the averaged, corresponding negative logmio GAl values for 4a and 5, respectively: CCRF-CEM (5.37, 5.77); HL-60 (TB)(5.51, 5.27); K-562 (5.13, 5.36); MOLT-4 (5.31, 5.72); RPMI-8226 (5.07, 5.21); SR (5.47, 5.42); A549/ATCC (5.46, 5.06); HOP-62 (5.27, 5.12); HOP-92 (5.02, 5.09); NCI-H226 (5.15, 5.10); NCI-H460 (5.52, 5.12); NCI-H522 (5.41, 5.38); COLO 8226 (5.07, 5.21); SR (5.47, 5.42); A549/ATCC (5.46, 5.06); HOP-62 (5.27, 5.12); HOP-92 (5.02, 5.09); NCI-H226 (5.15, 5.10); NCI-H460 (5.52, 5.12); NCI-H522 (5.41, 5.38); COLO 205 (5.23, 5.09); KM 12 (5.31, 5.04); SW-620 (5.44, 5.16); SF-268 (5.20, 5.02); SF-295 (5.44, 5.05); SF-539 (5.32, 5.24); SNB-75 (5.32, 5.25); U251 (5.49, 5.19); LOX IMVI (5.39, 5.48); MALME-3M (6.21, 6.41); SK-MEL-5 (5.96, 5.09); UACC-62 (5.60, 5.01); IGROV1 (5.14, 5.07); OVCAR-3 (5.74, 5.44); OVCAR4 (5.28, 5.74); OVCAR-8 (5.06, 5.37); 786-O (5.23, 5.21); ACHN (5.02, 5.10); RXF-393 (5.31, 5.28); SN12C (5.21, 5.15); PC-3 (5.70, 5.04); MCF7 (5.33, 5.09); MCF7/ADR-RES (5.34, 5.17); MDA-MB-231/ATCC (5.06, 5.57); HS578T (5.20, 5.06); MDA-MB-435 (5.74, 5.74); MDA-N (5.72, 5.66); T-47D (5.19, 5.68).

TABLE III $GI_{50}$ Results (μg/ml) for Various Cancer Cell Lines.

| Cell Type | Cell Line | Cribrostatin 3 | Cribrostatin 4 | Cribrostatin 5 |
|---|---|---|---|---|
| Pancreas-a | BXPC-3 | >1 | 5.6 | 0.29 |
| Neuroblast | SK-N-SH | — | 3.6 | — |
| Ovarian | OVCAR-3 | 0.77 | 2.2 | 0.18 |
| CNS | SF-295 | >1 | >10 | 0.36 |
| Thyroid ca | SW-1736 | — | >10 | — |
| Lung-NSC | NCI-H460 | >1 | >10 | 0.22 |
| Colon | KM20L2 | >1 | >10 | 0.14 |
| Pharynx-sq | FADU | — | 0.26 | |
| Prostate | DU-145 | >1 | >10 | 0.30 |
| Mouse Leukemia | P388 | 2.49 | 24.6 | 0.045 |

Testing of Compounds for Antimicrobial Activity New compounds cribrostatin 3, 4 and 5 were tested for antimicrobial activity in certain known test protocol and the results compared with results previously obtained for cribrostatins 1 and 2. The results are set forth in Table IV, below.

TABLE IV

Antimicrobial Activities of Cribrostatin 1 (1), Cribrostatin 2 (2a), Cribrostatin 3 (4a), Cribrostatin 4 (5) and Cribrostatin 5 (4b).

| | Minimum inhibitory concentration (μg/disk) | | | | |
|---|---|---|---|---|---|
| Microorganism | 1 | 2a | 4a | 5 | 4b |
| *Candida albicans* (ATCC 90028) | * | 3.12–6.25 | * | * | * |
| *Cryptococcus neoformans* (ATCC 90112) | * | 12.5–25 | * | * | * |
| *Micrococcus luteus* (Presque Isle 456) | * | 50–100 | * | * | 50–100 |
| *Staphylococcus aureus* (ATCC 29213) | * | 12.5–25 | * | * | * |
| *Enterococcus faecalis* (ATCC 29212) | * | * | * | * | * |
| *Bacillus subtilis* (Presque Isle 620) | * | 25–50 | * | 12.5–25 | * |
| *Streptococcus pneumoniae* (ATCC 6303) | * | 12.3–25 | * | 6.25–12.5 | * |
| Penicillin-resistant *S. pneumoniae* (clinical isolate) | NT[b] | 25–50 | NT | 50–100 | NT |
| Invasive *S. pneumoniae* (clinical isolate) | NT | 50–100 | NT | * | NT |
| Group A Streptococcus (clinical isolate) | NT | * | NT | 12.5–25 | NT |
| *Stenotrophomonas maltophilia* (ATCC 13637) | * | * | * | * | * |
| *Escherichia coli* (ATCC 25922) | * | * | * | * | * |
| *Enterobacter cloacae* (ATCC 13047) | * | * | * | * | * |
| *Neisseria gonorrhoeae* (ATCC 49226) | 0.39–0.78 | 0.39–0.78 | 0.0975–0.195 | 6.25–12.5 | 6.25–12.5 |
| Penicillin-resistant *N. gonorrhoeae* (clinical isolate) | 0.39–0.78 | 0.39–0.78 | 0.39–0.78 | 1.56–3.12 | 6.25–12.5 | a*-No inhibition at 100 μg/disk b NT = not tested

From the foregoing, it becomes readily apparent that a new and useful compounds have been herein described and illustrated which fulfill all of the aforestated objectives in a remarkably unexpected fashion. It is of course understood that such modifications, alterations and adaptations as will readily occur to the artisan confronted with this disclosure are intended within the spirit of the present invention.

What is claimed is:

1. In substantially pure form substance having the structural formula:

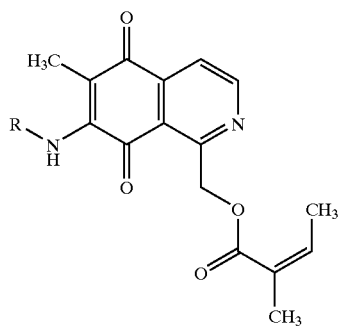
in which R is either H or CH₃.
2. A substance in substantially pure form according to claim 1 denominated cribrostatin 3.
3. A substance in substantially pure form according to claim 1 denominated cribrostatin 5.
4. A substance in substantially pure form having the structural formula:
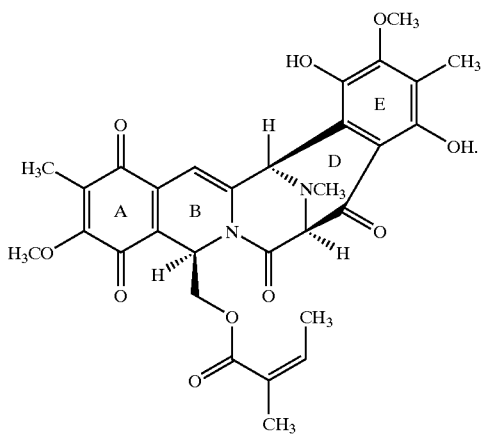
* * * * *